United States Patent
Robrahn et al.

[11] Patent Number: 6,138,286
[45] Date of Patent: Oct. 31, 2000

[54] GOGGLE HAVING A TINTED PLASTIC LENS

[75] Inventors: David T. Robrahn, Ketchum, Id.; Robert Youmans, Vashon, Wash.; Etienne Billard, Saint Claude; Christine Bejannin, Vaux les Saint Claude, both of France

[73] Assignees: Scott USA, Inc., Ketchum, Id.; Christian Dalloz Sunoptics, Sainte-Claude Cedex, France

[21] Appl. No.: 09/291,711

[22] Filed: Apr. 14, 1999

[51] Int. Cl.[7] .................................................. A61F 9/02
[52] U.S. Cl. ...................... 2/436; 2/426; 2/443; 351/44
[58] Field of Search ................... 2/426, 432, 441, 2/443, 428; 351/44, 47, 163

[56] References Cited

U.S. PATENT DOCUMENTS

| | | |
|---|---|---|
| 1,741,536 | 12/1929 | Rayton . |
| 3,517,393 | 6/1970 | Beauchef ................................. 2/426 |
| 3,718,937 | 3/1973 | Smith . |
| 3,945,044 | 3/1976 | McGee et al. . |
| 4,271,538 | 6/1981 | Montesi et al. . |
| 4,653,124 | 3/1987 | McNeal et al. . |
| 4,952,046 | 8/1990 | Stephens et al. . |
| 5,177,509 | 1/1993 | Johansen et al. ....................... 351/44 |
| 5,341,516 | 8/1994 | Keim ...................................... 2/452 |
| 5,363,512 | 11/1994 | Grabos, Jr. et al. . |
| 5,400,175 | 3/1995 | Johansen et al. . |
| 5,408,278 | 4/1995 | Christman ............................. 351/44 |
| 5,438,024 | 8/1995 | Bolton et al. . |
| 5,546,611 | 8/1996 | Lathrop .................................. 2/428 |
| 5,805,263 | 9/1998 | Reymondet et al. . |
| 5,922,246 | 7/1999 | Matsushita et al. ................. 252/582 |
| 5,926,310 | 7/1999 | Tamura et al. ...................... 359/350 |
| 5,975,695 | 11/1999 | Baiocchi et al. ..................... 351/163 |
| 5,997,139 | 12/1999 | Yasuda .................................. 351/49 |

OTHER PUBLICATIONS

"ChroMax B20, Un Nouveau Verre Pour Bausch & Lomb", L'Opto No. 55, May 1994, pp. 32–35.
Advertisement "Le Verre ChroMax Pour Une Conduite Optimale".
Advertisement "The World's Most Advanced Driving Sunglass" Ray–Ban ChroMax Lens.
"Light", author Michael I. Sobel, The University of Chicago Press, 1987, 1989, cover page, copyright page, pp. 34–37 and 49–61.
"Colour Why the World Isn't Grey", author Hazel Rossotti, Princeton University Press, 1983, 1985, cover page, copyright page, pp. 109–121.

*Primary Examiner*—John J. Calvert
*Assistant Examiner*—Katherine Moran
*Attorney, Agent, or Firm*—Ronald L. Wanke; Jenner & Block

[57] ABSTRACT

A goggle has a replaceable plastic lens mounted in a flexible frame containing several air vents for passing external air through the goggle interior. The lens is formed of thermoplastic materials to provide spherical and cylindrical versions of the lens. The thermoplastic resins incorporate dyes which tint the lens to create transmission curves having peaks and valleys which approximate or enhance certain response characteristics of the retina of the human eye. Inlet air vents are covered by porous foam located in an upper air channel to disperse downwardly the external air into the interior space behind the lens. Outlet vents located in the bottom of the frame are covered with a porous foam to exit air from the interior space.

38 Claims, 3 Drawing Sheets

GOGGLE HAVING A TINTED PLASTIC LENS

TECHNICAL FIELD

This invention relates to a goggle having plastic lenses which can be tinted to affect contrast and vision characteristics. It has applicability to goggles used in an outdoor or other adverse environment, such as a sports goggle or a safety goggle.

BACKGROUND OF THE INVENTION

Goggles which are intended for use in an outdoor or other adverse environment include sports goggles such as for skiing or motorcycle use, as well as safety goggles. Such goggles provide protection for the wearer's eyes from external air and particulate matter. The goggles may have vent apertures open to external air flow to exchange air between the exterior environment and the interior of the goggle. Such a vented exchange of air will minimize fogging caused by moisture in the air condensing on the lens of the goggle. The vent apertures are typically covered by a porous foam to control the air exchange while forming a partial barrier to snow, dust and other particulate matter. The goggles also include replaceable plastic lenses which may be a single lens or a double lens, and such lenses can be tinted in various colors to assist in contrast and glare protection.

While certain improved contrast resolution capabilities have been available in fixed glass lenses for eyeglasses and sunglasses, there is a need for improved contrast resolution capabilities which are specifically adapted to plastic lenses for goggle use. In the case of a sports goggle or safety goggle, for example, there is a need for a plastic lens which is lighter and more shatter-resistant than glass but which has improved contrast resolution over a wide variety of light conditions. In particular, it is desirable to provide a plastic lens for a goggle which has improved contrast resolution in low light conditions in which it is difficult to distinguish between adjacent surface areas which are partially in shadow conditions. Such adverse conditions in a sports goggle such as a ski goggle can result from snow and fog which create whiteout conditions, whereas such conditions in a safety goggle can result from heavy particulate matter in the air.

High contrast resolution is desirable in plastic spherical lens of variable thickness such as formed by injection molding of polycarbonate material. In addition, the availability of high contrast resolution is desirable for a thermoplastic lens stamped from flat sheets of extruded resin, such as cellulosics, which form a cylindrical goggle lens. Furthermore, such thermoplastic lenses desirably are removably mounted such as in a peripheral groove of a flexible injection molded plastic frame for a sports goggle or a safety goggle. Furthermore, there is a need in a goggle to better coordinate the plastic lens materials, dyes and coatings with venting capabilities of a vented goggle to improve the overall anti-fogging and vision properties of the goggle.

SUMMARY OF THE PRESENT INVENTION

A goggle is provided which overcomes certain of the problems and disadvantages of prior goggles. Many of its features have utility when a goggle is worn in conjunction with a helmet or protective headgear, although the goggle is not limited to use with a helmet or headgear. Other features overcome problems associated with goggles intended to be used in a high speed sport, as well as problems associated with the outdoor environment which is more prone to a wide variety of light and atmospheric conditions, including lack of contrast between adjacent surfaces in certain low light adverse conditions.

In one aspect, the invention has particular utility for goggles having a removable plastic lens which is tinted in a manner to improve contrast resolution for a wide variety of light levels and light characteristics including certain adverse conditions. The tint is adapted to the plastic materials usable in goggle lenses to provide a goggle having improved visual performance and anti-fogging characteristics. In particular, the tint creates a transmission curve characterized by peaks and valleys along the visible wavelength spectrum which conforms to certain characteristics of the human eye to improve contrast in a plastic lens. Such a plastic lens is particularly useful when it is removable and can be replaced as necessary.

In a related aspect, the invention has particular utility for goggles formed of a flexible frame which surrounds the wearer's eyes and is used in conjunction with a removable plastic lens. Such a goggle can be adapted to an outdoor environment having adverse condition. Such a goggle frame may be vented and include vent openings covered by porous foam for exchanging air within the goggle interior in a manner which reduces fogging or condensation on the interior of a plastic tinted lens having various coatings for anti-fogging purposes. Such vented goggles are particularly adaptable to a sports environment such as winter sports or motorcycling, but also have applicability to a safety goggle.

A better understanding of the present invention along with other objects and advantages will become apparent from the following description and with reference to the following drawings.

DESCRIPTION OF THE PREFERRED EMBODIMENTS

Figure 1:
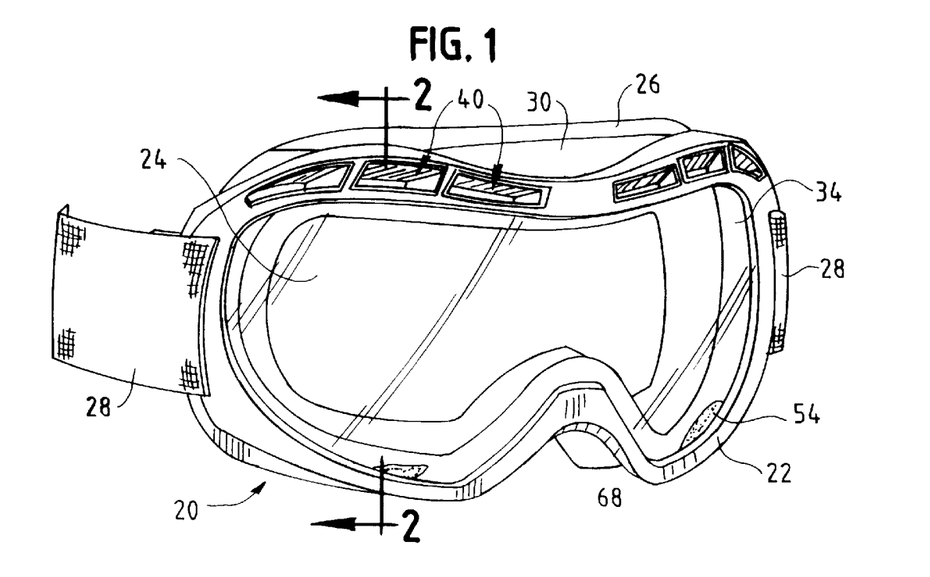
FIG. 1 is a perspective view of a novel goggle including a novel plastic lens.

As seen in the drawings, a goggle 20 which is particularly useful in an outdoor environment, although not limited thereto, includes a plastic flexible frame 22 which surrounds the eye region of a wearer. A front lens 24 of plastic material is removably mounted at the forward area of the surrounding frame 22 in order to protect the wearer's eyes. A flexible face padding 26 is glued or otherwise affixed to the rear of the frame 22 in order the cushion the frame against the face of the wearer and create a partial seal against the wearer's face. An elastic headband strap 28 attaches to both sides of the frame 22 to secure the goggle to the wearer's head or to the back of a helmet, as appropriate. Typically, the strap 28 will include a buckle adjustment (not illustrated) in order to vary the length of the strap 28 so as to secure the goggle relatively snugly against the face of the wearer.

The flexible frame 22 includes a top portion 30, a bottom portion 32, and side portions 34 which are injection molded as one piece from a thermoplastic resin such as polycarbonate which results in a molded pliable frame which is relatively stiff as is conventional in vented sports goggles. The frame surrounding portions in conjunction with the front lens 24 defines an interior space 36, see FIG. 2, when the goggle is placed against the wearer's face.

Figure 2:
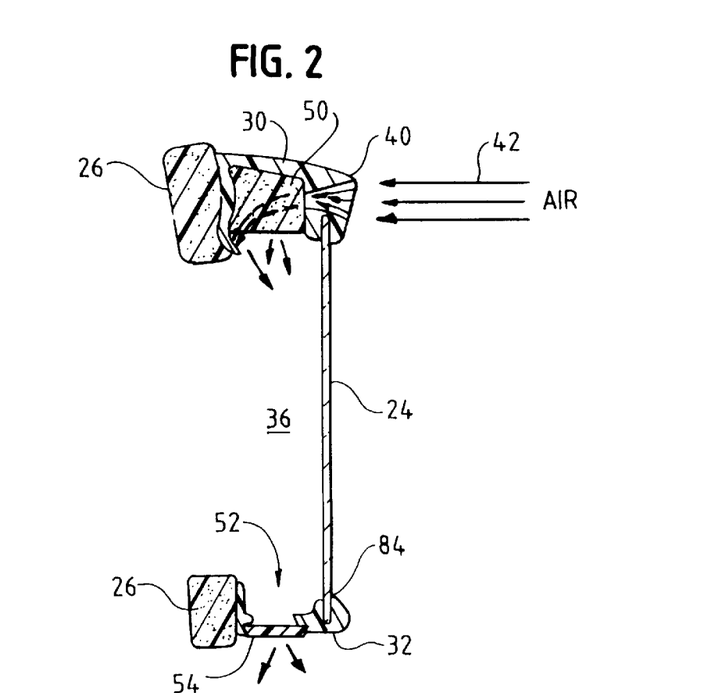
FIG. 2 is a side cross-sectional view of the goggle taken along lines 2—2 of FIG. 1.

As is seen best in FIGS. 1–2, the top portion 30 of the goggle frame is solid and has a generally smooth and planar extent, which can dip in the center. This smooth, solid, top surface forms a helmet contacting or mating surface for use when the goggle is worn in conjunction with a helmet. There are no vent apertures or other openings in the top portion 30. When a helmet is worn, the top planar surface will mate with and contact the helmet or helmet padding, in order to form a partial seal between the goggle top where it abuts the helmet. As a result, the goggle is particularly adapted for use with a helmet, although it is not limited to such use. The frame side portions 34 and/or bottom portion 32 have a variety of air vents located therein, for purposes of exiting air flow out of the goggle interior.

Along an elongated front upper section of the frame, beneath the top portion 30, a plurality of forward facing air scoops or air vents 40 are located to directly receive air as the wearer moves relatively in a forward direction. This frontal air, illustrated by the arrows 42 in FIG. 2, enters the forwardly facing air scoops 40 in large volumes compared to conventional goggles. The frontal air 42 is funneled through the inlet vent scoops 40 and into an upper chamber enclosed along its top and side and open downwardly to channel the frontal air into the goggle interior region 36. This upper chamber includes means for dispersing the air flow generally downward and with a forward component to improve interior venting of the goggle, but without rapid air flow across the wearer's eyes which could otherwise result if the forward-facing vents 40 directly communicated with the goggle interior.

The mechanism which redirects and disperses the forward air flow in a controlled manner includes the shape of the upper chamber 44 and, in addition, a permeable foam 50 located in the upper chamber 44. This foam 50 is of a porosity and size so as to redirect the air flow with reduced velocity and dispersement into the interior space 36 of the goggle.

In one embodiment, the foam 50 is a thick foam which may take all or substantial portion of the volume of the upper chamber. The dimensions of such foam can be approximately 16 mm by 16 mm by the longitudinal length of the upper chamber. The foam strip should be in intimate contact with the exit openings of the plurality of air scoops 40. It is formed of an open cell foam having a porosity of 20 to 80 pores per inch (ppi).

The air flow from the combination of the foam 50 and the upper air chamber moves in a generally downward direction through the interior space 36 and partly against the inside of the front lens 24. This air moves towards a plurality of exit vents 52 located in the frame bottom 32. The outlet vents 52 are formed as one or a plurality of apertures in the goggle frame. Preferably, the exit vents 52 are located in the bottom section 32 of the goggle frame so as to draw air from the top of the frame downwardly to exit at the bottom of the frame in the vicinity of the nose region. This serves to disperse moisture-laden air from the wearer's nose and thus assist in reducing fogging within the goggle. However, the exit apertures 52 also can be located in the side regions of the frame, in place of or in addition to the exit vents in the bottom section.

The exit vents 52 are covered with a thin permeable foam strip 54 which can be of 3 mm thickness and having an open cell porosity of 80 ppi. Preferably, the foam 50 associated with the inlet of air is different than the foam 52 associated with the exit of air to better control movement of air through the goggle interior.

A goggle of the type illustrated in FIGS. 1 and 2 is shown in more detail and various aspects are claimed in a co-pending application of certain of the inventors herein, entitled "Goggle For Sports and Adverse Environments," inventors David T. Robrahn and Robert Youmans, and filed on Mar. 5, 1999. The contents of said co-pending application of Robrahn et al. are hereby incorporated by reference into this application, and reference should be made to such co-pending application for further explanation about the various mechanical features of the goggle which can be used in conjunction with the present invention.

Figure 3:
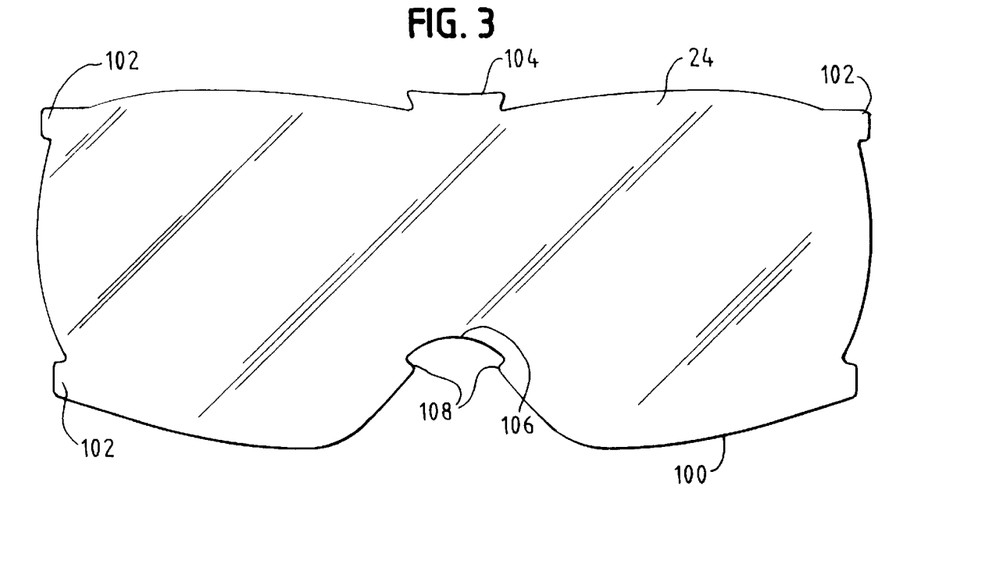
FIG. 3 is a front plan view of the removable plastic lens of the goggle of FIGS. 1 and 2.

As seen in FIGS. 2 and 3, the front lens 24 is formed of a plastic material and has a peripheral edge 100 of irregular shape which is inserted in a surrounding groove 84 of the frame for removable retention within the frame. The lens edge 100 includes projections for mating engagement with corresponding recesses in the peripheral groove 84. The lens projections include side ears 102 on each side of the lens 24, and a central upper tab 104. The lens 24 has a recessed nose area 106 which is received within a center nose bridge 68 of the goggle frame so that the interior space 38 surrounds the eyes of the wearer but does not encompass the wearer's nose. The recessed nose area 106 has projections 108 which serve as a notch to mate within recessed areas of the peripheral groove 84 to better retain the center portion of the lens within the goggle frame.

The lens 24 is replaceably mounted within the peripheral groove 84 by manipulating the flexible frame 22 so as to insert the peripheral edge 100 within the surrounding groove 84. When inserted, the various projections 102, 104, 108 extend into mating recesses within the peripheral groove 84 to assist in retaining the replaceable lens 24 within the goggle frame.

The plastic lens 24 is formed from a thermoplastic resin and may be formed as a spherical lens in order to have the best optical properties or as a cylindrical lens. Thermoplastic resins are linear polymers which can be melted and resolidified. Examples of suitable thermoplastic resins for the lens 24 are polycarbonate (PC) as well as the cellulosic family, as will be described.

In the spherical lens embodiment, the plastic lens 24 is formed out of a polycarbonate (PC) material which is injection molded into a three-dimensional shape having an arcuate curve from top 104 to bottom 106 along its minor axis, and additionally an arcuate curve along its major axis from one side to the other side. In addition, the lens 24 has a thickness which varies from the center region(s) to its edge 100. For example, in one preferred embodiment, the lens has a maximum thickness of about 1.5 mm or less, such as 1.3 mm, which tapers to a thickness of 0.9 mm at the peripheral edge 100. The radii of curvature from top to bottom and side to side create an overall spherical shape with a varying thickness. Such a spherical lens is of very low weight and has good optical properties because it does not create any magnification or distortion. The resulting hard plastic lens will maintain its shape and has better optical qualities and impact resistance than a cylindrical plastic lens, albeit at an increased cost of production.

In another embodiment, the replaceable plastic lens 24 can be formed of several cellulosic thermoplastic resins based on cellulose, a complex carbohydrate chemically modified to produce a plastic. This cellulosic material is extruded flat with a constant thickness. Then, the lens is stamped out of the flat sheet so as to have the shape illustrated in FIG. 3. The use of a cellulosic material produces a flexible lens of low cost and reasonable quality. However, it is possible to use a polycarbonate material which is extruded flat. In either version, the resulting lens is flat of constant thickness and is flexible. When inserted into the peripheral groove 84, such a lens will curve from side to side following the curved shape of the frame 22, and hence is referred to as a cylindrical lens. Such a cylindrical plastic lens can be produced at relatively low cost and is satisfactory for many applications, although it does not have the superior optical qualities nor impact resistance of a hard lens of polycarbonate which is injection molded in spherical form as previously described.

The replaceable plastic lens 24, whether produced in the spherical embodiment or in the cylindrical embodiment, is desirably tinted or colored by pigment dyes incorporated into the thermoplastic resin to produce transparent colors to create a high contrast resolution lens. The composition of the dyes will vary depending on the composition of the plastic lens 24. The resulting lens tint will be referred to at times hereinafter as "HC" for high contrast tint. The HC tinted lens desirably has a transmission curve with an undulating or wavy shape which should approximate the sensitivity of the human eye to light of various wavelengths for the intended conditions of use of the goggle, as will be explained.

The human eye contains photoreceptors which are located in the retina. There are two types of photoreceptors, rods which primarily determine night vision and cones which provide high acuity (definition) and color vision in daytime light conditions. There are three types of cones in the retina of the human eye, each having a different pigment and different absorption curves. One set of cones is particularly receptive to blue light in the vicinity of about 400 to 450 nm, another set of cones is receptive to the absorption of green light around 525 to 575 nm, and the third set of cones is particularly susceptible to red or orange-red light in the vicinity of 550 to 600 nm. There is substantial overlap of these absorption curves and a broad range of wavelengths are absorbed to some extent by the pigments of all photoreceptors. Both rods and cones function to some degree at all times.

The responses of rods and cones both contribute to vision at intermediate and other low-level intensities of illumination. Furthermore, the human eye response is not directly related to the peaks of wavelengths per se, but rather to an integration of the spectral curve and relative ratios of intensities of the pigments of the cones and rods. At times only two cones are essentially effective. As light intensity falls, the human eye becomes increasingly sensitive to light of shorter wavelengths. At low light conditions such as twilight the eye is most sensitive to a blue-green light such as 510 nm. The HC tint for the lens 24 desirably approximates the response curves for cone photoreceptors in the retina, but with certain modifications to enhance the use of the goggle for certain conditions. Desirably, the goggle lens takes advantage of the shift to shorter wavelengths in low light conditions by modifying the transmission curve of the lens so as to be more efficient in low light conditions such as by enhancing the response to blue light.

In general, the combination of pigments to be used will vary depending on the thermoplastic resin used for the lens 24. Various dyes should be combined so as to approximate to a reasonable extent and at a reasonable cost a spectral curve such that wavelengths less useful to the human retina are reduced in magnitude while wavelengths more useful to the human retina are transmitted in greater quantities. In certain preferred embodiments, the spectral curve is enhanced in the blue light region so as to improve the coupling of transmitted light to the retina for improved resolution in low light conditions.

More particularly, the plastic lens 24 is desirably formed of a transparent thermoplastic resin which incorporates dye material so as to tint the lens to transmit an average percentage of light over a wide bandwidth, and to pass selected wavelengths and diminish other wavelengths so as to create a response curve better correlated to the photoreceptors of the eye. By way of example, the lens 24 when used in a ski goggle should reduce the transmission of visible light to the eyes on bright sunny days. It should optimize contrast for overcast conditions. The lens should have a high optical quality and a high impact resistance. It should resist fogging. It should be comfortable under prolonged use and be durable. It is also desirable that it absorb as much as possible of ultraviolet (UV) radiation.

Plastic lens 24 can be designed as a universal lens adaptable for a wide variety of lighting levels, or can be designed as multiple lenses each designed for a particular level of light. In one preferred form, it was designed as a universal lens for a goggle used in an outdoor environment and this necessitates a compromise for various properties of the lens. If overall light transmission is too high, the eyes will become strained under prolonged use in bright sunlight. If light transmission is too low, contrast will be poor in low light conditions. A desirable range of average light transmission to the eye for such a universal lens is about 25% to 40%. For a single lens, an average light transmission of 35% plus or minus 3% is acceptable. To form a double lens, the same outer lens may be utilized in combination with a clear inner lens, which reduces average transmission about 10%, so the resulting average transmission is about 25% to 27% to the eye.

Another important factor is to provide a high contrast or "HC" lens tint which will improve contrast resolution in low light conditions. For example, in a sports goggle 20 for skiing or snowmobiling, it is desirable that the lens 24 improve contrast between undulations or shadows and a surrounding snow surface in overcast conditions. Therefore, dye material is incorporated into the lens to produce a tint which selectively transmits wavelengths that approximate the absorption wavelengths of the cone photoreceptors including the blue cone receptors.

Figure 4:
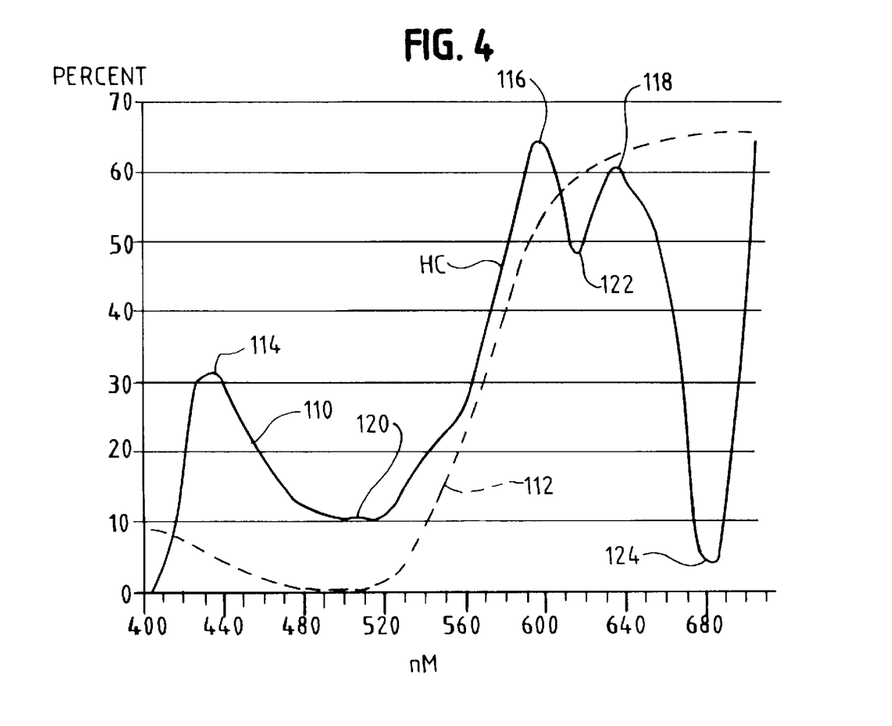
FIG. 4 is a transmission curve or spectral curve for one embodiment of the plastic goggle lens and showing light transmission versus wavelength for the one embodiment as well as a prior art plastic goggle lens.
Figure 5:
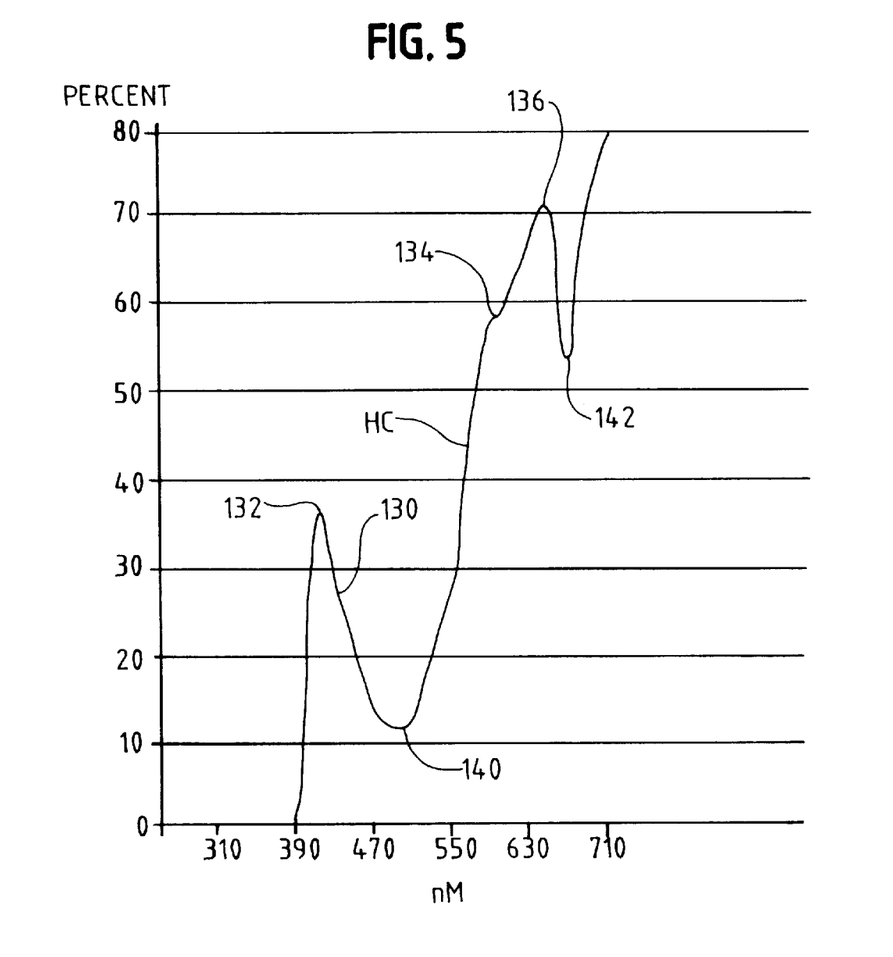
FIG. 5 is a transmission curve or spectral curve for a second embodiment of the plastic goggle lens and showing light transmission versus wavelength for the second embodiment.

In FIGS. 4 and 5, transmission curves or spectral curves are illustrated for tinted thermoplastic lenses formed of different materials and dye pigments. In FIG. 4, a transmission curve 110 is shown for an HC tinted polycarbonate lens. This can be compared with the transmission curve for a standard tint cellulosics lens, such as a sienna tint of yellow-orange color, illustrated by the dashed lines. In FIG. 5, the transmission curve 103 for an HC tinted cellulosics lens is illustrated. For all transmission curves, the percentage (%) of light transmission through the lens is given for various visible wavelengths of light in nanometers or "nm," extending from 400 nm to about 700 nm.

The transmission curve 110 for an HC tinted polycarbonate lens can be produced by incorporating dopants or pigments into the polycarbonate resin prior to injection molding. For example, the HC tint may be obtained from a blend of three pigments, namely a white/yellow pigment to give superior filtration in the 400 nm range, a red pigment, and a blue pigment. The red and blue pigments have a major function in the filtration of the visible light. The quantity of pigments needed depends on the average filtration level that is required, the concentration of the pigments, and the thickness of the lens. By way of example, a ratio suitable for the HC tint seen in the transmission curve 110 is approximately 10 parts for the red pigment compared to one part for the blue pigment.

The quantities of pigment added into the polycarbonate material are measured in parts per million or ppm. According to the different thickness of the lens in association with the filtration levels, the quantities may vary from less than 10 ppm to more than 200 ppm. As a particular example for a 35% average transmission, the concentration can be 27 ppm for blue pigment and 272 ppm for red pigment. Variations in the pigment levels and tolerances will have an influence on the transmission level, as follows.

For a polycarbonate lens formed of a single sheet and having an average transmission of light in the range of about 32% to 38%, this difference in transmission represents a relative transmission increase of about 19%. This can be achieved by a 15% decrease in the concentration of pigment. Moreover, the variation will depend in part on thickness differences from one lens to another. As another example, if a lens is formed having an average transmission of light in the range of about 25% to 27%, this represents a relative increase of about 8% transmission. This can be achieved by a 5.5% decrease in the concentration of pigment. Again, there will be a variation depending on the thickness differences in the lenses.

By way of example, a blend of three pigments as described above to produce the transmission curve 110 seen in the drawings is available as the 61324 tint from Christian Dalloz Sunoptics of Saint-Claude, France, the assignee of certain of the inventors of the present application. The properties of the tint pigments are such when incorporated into polycarbonate resin as to produce the transmission curve 110 of FIG. 4 with three peaks 114, 116 and 118 of increased transmission located at approximately 430 nm, 590 nm and 630 nm, respectively. Between peaks 114 and 116 is a valley 120 of reduced transmission which flattens at the area of 510 nm or so. A second valley 122 of reduced transmission is located between peaks 116 and 118 in the vicinity of 610 nm, and a third valley 124 follows the peak 118 at about 680 nm.

The peak 114 in the vicinity of 430 nm corresponds fairly closely to the peak absorption curve of the blue cone receptors of the human eye. Furthermore, the peak 114 has a light transmission level desirably greater than 20%, such as about 30%. This is followed by a substantial dip to a valley 120 at about a 10% transmission level in the vicinity of 480 to 520 nm. Preferably, the blue response peak 114 is desirably twice to three times the transmission level of the valley 120. While reference is made to the relative heights of the peaks and valleys, it should be understood that the eye will integrate the area under the curve. The peak 114 produces good coupling to the blue cones of the eye and improves contrast in low light conditions.

The curve 110 of FIG. 4 then has peaks 116 and 118 which each transmit about 60% and are separated by the valley 122 at less than 50% transmission. These peaks and valleys are somewhat transposed from the green and red cone receptors, but nonetheless are reasonably optimized to absorb light wavelengths of more utility to the cone receptors of the human eye.

The transmission curve for a conventional tinted cellulosics lens is illustrated by the dashed line curve 112 which is for a sienna or yellow-orange tint. The curve 112 has a slight rise between 400 nm to 480 nm, but with a less than 10% transmission value, the curve can be considered essentially flat. The curve 112 in the vicinity of 500 nm begins a continuous upward slope without pronounced peaks and/or valleys. Such a smooth curve does not couple efficiently to the characteristics of the human eye.

More particularly, the following Table 1 lists the percent (%) transmission of light for wavelengths in nm for the novel HC tint 110 incorporated into a polycarbonate lens and for a standard sienna tint incorporated into a cellulosics lens.

TABLE 1

| Wavelength | HC Tint | Sienna Tint |
|---|---|---|
| 400 | 0.0% | 8.8% |
| 410 | 8.1% | 8.2% |
| 420 | 29.1% | 6.6% |
| 430 | 31.6% | 4.9% |
| 440 | 25.5% | 3.3% |
| 450 | 20.7% | 2.2% |
| 460 | 16.1% | 1.5% |
| 470 | 12.8% | 0.8% |
| 480 | 11.3% | 0.6% |
| 490 | 10.6% | 0.6% |
| 500 | 10.6% | 0.6% |
| 510 | 10.4% | 1.1% |
| 520 | 12.4% | 2.8% |
| 530 | 17.5% | 7.1% |
| 540 | 21.2% | 12.8% |
| 550 | 24.5% | 18.9% |
| 560 | 31.1% | 26.5% |
| 570 | 41.4% | 35.3% |
| 580 | 53.1% | 44.1% |
| 590 | 64.4% | 51.4% |
| 600 | 60.9% | 56.5% |
| 610 | 48.3% | 59.5% |
| 620 | 54.8% | 61.6% |
| 630 | 60.7% | 62.8% |
| 640 | 56.1% | 63.7% |
| 650 | 51.3% | 64.2% |
| 660 | 35.7% | 64.7% |
| 670 | 6.7% | 65.1% |
| 680 | 4.6% | 65.5% |
| 690 | 26.8% | 65.7% |
| 700 | 64.2% | 66.1% |

While the above Table 1 and transmission curve of FIG. 4 illustrate one preferred embodiment for an HC tinted lens, it should be understood that the transmission curve can be varied and the peaks and valleys do not have to be as pronounced as illustrated nor in the same locations. For example, a lesser number of peaks and/or valleys can produce generally satisfactory results, but with some degradation in perceived contrast resolution.

In FIG. 5, the transmission curve 130 represents one embodiment for a cellulosics lens 24. This lens was produced by attempting to color match a tinted polycarbonate lens having the transmission curve 110 of FIG. 4. The difference in the absorption bands between curves 110 and 130 are attributed in part to the use of a cellulosics lens rather than a polycarbonate lens as well as different dye pigments. The HC tint for a cellulosics lens is available as Z0705 orange pigments from Polymer Extruded Products, Inc. of Newark, N.J., and the pigments were produced by Eastman.

The resulting curve 130 is less satisfactory than the curve 110 of FIG. 4, but it does produce a better coupling to the cone receptors of the retina than prior art tints such as incorporated in a cellulosics lens. As seen in FIG. 5, the HC tint 130 produces three peaks 132, 134 and 136. The first peak 132 has a maximum transmission of about 35% located in the blue color range between 410 to 430 nm. The blue peak 132 then sharply drops to a valley 140 having transmission of 12% to 15% or so. Desirably there is a two to three times difference in transmission level between the first valley 140 and the first peak 132. The transmission curve 130 then rises to a plateau 134 of near 60% transmission in the area of 590 to 610 nm. Unlike the polycarbonate lens, there is no valley following the second peak 134 but rather the curve rises to a third peak 136 near a 70% transmission level at 630 to 650 nm. The last peak is then followed by a second valley 142 of reduced transmission of at least a 10% drop, such as about a 55% transmission level.

In the spherical lens embodiment, the plastic lens 24 is desirably formed from a polycarbonate (PC) material which is injection molded to create a hard lens blank having a varying thickness. To create an overall spherical geometry or shape, the lens blank may have multiple radii to reduce distortion. Examples of spherical lens shapes and a process of manufacturing lens blanks are illustrated in U.S. Pat. No. 1,741,536 to Rayton entitled "Goggles," issued Dec. 31, 1929, U.S. Pat. No. 4,271,538 to Montesi et al., entitled "Safety Spectacles," issued Jun. 9, 1981, and U.S. Pat. No. 5,805,263 to Reymondet et al., entitled "Lens Blanks, Process Of Manufacture Therefor And Eyewear Incorporating Lenses Made Therefrom," issued Sep. 8, 1998 and assigned to one of the joint owners of this application, the disclosures of which are hereby incorporated by reference herein. The blank may be stamped or cut with a peripheral edge shape as illustrated in FIG. 3 by a lens manufacturer in order to produce a replaceable lens member usable with a goggle. Alternatively, the lens blank can be supplied to a goggle manufacturer who can then die cut the lens blank into the appropriate shape to form the replaceable lens member for the goggle. The resulting PC lens member will have a high impact resistance as is desirable for sports goggles and safety goggles. The PC lens may be treated with a coating in order to improve scratch resistance.

In the cylindrical lens embodiment, the plastic lens 24 is preferably made out of the cellulose family. In particular, the lens can be formed from cellulose acetate (CA), cellulose acetobutyrate (CAB), or cellulose acetopropionate (CAP). Typically, these cellulosics are compounded with plasticizers and are then extruded into a flat sheet of constant thickness. The optical quality of the flat sheet can be improved by placing the cellulosic sheet between chemically polished metal sheets and then pressing the laminate at high pressure and temperature, in a process known as press polishing. This improves the optical clarity of the sheet and reduces surface defects that will impair vision. The resulting cellulosic lens member can then be cut or stamped so as to have the peripheral edge shape of FIG. 3 in order to form a replaceable lens for a goggle.

The goggle lens 24 when made from cellulosics material such as CAB, CAP, or CA, has a lower impact resistance than the spherical lens made of polycarbonate but with a sufficient impact resistance to be used in a more inexpensive goggle. The impact resistance will vary with the amount of plasticizer added for processing. In general, the lens 24 when formed of CAP will have the highest impact resistance for a cellulosics lens, with CAP being a close second, and CA being considerably below CAP.

For use in an outdoor or adverse environment, it is desirable that the plastic lens 24 should resist fogging caused by an increase in relative humidity in the interior space 36. The venting of the goggle interior through the inlet vents 40 and outlet vents 52 assists to reduce the relative humidity. In addition, the lens 24 can be surface treated with an anti-fogging coating to cause water on the interior side of the lens to bead or form a film.

In particular, the plastic lens 24 when formed of cellulosic material is desirably treated by immersion into a solution that chemically treats both surfaces or at least the inner surface adjacent interior space 36. This treatment is done in sheet form prior to forming. The result is a surface that initially absorbs moisture until saturation, and then causes additional moisture to form as a film of water rather than beads. When the plastic lens 24 is formed of a polycarbonate material, an anti-fogging coating can be applied to one or both surfaces by dipping the lens into a solution. The result is a surface which tends to form beads of water on the treated side of the lens.

When the goggle is to be used in cold temperatures, the lens 24 can be of double lens construction, often referred to as a thermal lens. The outer lens can be a thin, injection molded, spherical lens of polycarbonate material which is hard-coated on both sides. The polycarbonate material is colored with the HC tint pigments described previously. The inner lens can be formed of clear cellulosic material such as CAP having for example a 0.025 inch thickness with an anti-fog treatment on one or both sides. To ensure preciseness in curvature, it should be thermoformed to match the inner radius of the outer PC lens. The inner and outer lens can be separated by a gasket spacer, such as a 0.125 inch thick foam with adhesive on both sides around the entire peripheral edge.

When the goggle is intended for use in the outdoor environment, it is also desirable that the plastic lens 24 absorb or block as much ultraviolet (UV) radiation as possible. In particular, it is desirable that the lens filter as much as possible of UV rays from 100 to 400 nm. The lens can have a conventional dye added in order to create a tint which will filter out most ultraviolet wavelengths up to about 380 nm.

Further modifications and changes to the invention can be made without departing from the scope of the invention.

What is claimed is:

1. A goggle comprising:

a frame having sections surrounding a wearer's face including a frame mounting section, a plastic lens formed of a thermoplastic resin and mountable in the frame mounting section in spaced relation in front of the wearer's face to define an interior space, the thermoplastic resin incorporating dye material to tint the plastic lens to transmit variable amounts of light over a range of wavelengths between 400 nm and 700 nm, the tinted plastic lens having a transmission curve with at least two separate peaks of increased transmission over said range and at least one valley of reduced transmission between the separate peaks to improve contrast for a wearer of the goggle, wherein one of said at least two peaks of increased transmission over said range is located in the vicinity of the blue absorption band for cone photoreceptors in a human eye retina.

2. The goggle of claim 1 wherein the thermoplastic resin is comprised of polycarbonate material which is injection molded to form the plastic lens.

3. The goggle of claim 2 wherein the polycarbonate material is injection molded into a spherical lens having a varying thickness from a center towards its edge.

4. The goggle of claim 1 wherein the thermoplastic resin is comprised of a cellulosic material which is extruded into a sheet which forms the plastic lens.

5. The goggle of claim 4 wherein the cellulosic material is extruded into a flat sheet of constant thickness, the frame mounting section having a curved shape, and the plastic lens being mountable therein to create a cylindrical lens of constant thickness.

6. The goggle of claim 1 wherein one of said at least two peaks of increased transmission is greater than 20% transmission is located in the vicinity of 400 nm to 450 nm.

7. A goggle comprising:
a frame having sections surrounding a wearer's face including a frame mounting section,
a plastic lens formed of a thermoplastic resin and mountable in the frame mounting section in spaced relation in front of the wearer's face to define an interior space wherein the plastic lens has an average transmission of light in the range of about 25% to 40%,
the thermoplastic resin incorporating dye material to tint the plastic lens to transmit variable amounts of light over a range of wavelengths between 400 nm and 700 nm, the tinted plastic lens having a transmission curve with at least two separate peaks of increased transmission over said range and at least one valley of reduced transmission between the separate peaks to improve contrast for a wearer of the goggle.

8. The goggle of claim 7 wherein the lens is a single lens having an average transmission of light in the range of about 32% to 38%.

9. The goggle of claim 7 wherein the lens is a double lens having an average transmission of light in the range of about 25% to 27%.

10. A goggle comprising:
a replaceable plastic lens formed of a thermoplastic resin and containing mounting projections,
a frame having sections surrounding a wearer's face including a lens mounting section for mating engagement with the mounting projections to replaceably mount the lens in spaced relation in front of the wearer's face to define an interior space,
the plastic lens having a tint producing a transmission curve for visible light with an average transmission through the lens in the range of about 25% to 40% and at least one peak of greater than 20% transmission for a first range of wavelengths between 400 nm and 680 nm followed by at least one valley of reduced transmission at a second range of wavelengths adjacent and above the first range.

11. The goggle of claim 10 wherein the transmission curve includes a second peak of greater than 20% transmission at a third range of wavelengths above the second range followed by a second valley of reduced transmission at a fourth range of wavelengths adjacent and above the third range.

12. The goggle of claim 11 wherein the one peak and one valley and the second peak and second valley pass light corresponding to the absorption bands of cones in a human eye retina so as to improve contrast resolution for visible light passing through the plastic lens.

13. The goggle of claim 10 wherein the first range of wavelengths is about 400 nm to 450 nm.

14. The goggle of claim 13 wherein the one peak has about a 30% transmission or greater for blue light of about 400 nm to 450 nm.

15. The goggle of claim 14 wherein the one valley has a 15% transmission or less for light in the second range of wavelengths adjacent blue light.

16. The goggle of claim 10 wherein the transmission curve has a wavy shape with peaks and valleys related to the absorption bands of cones in a human eye retina to thereby improve contrast resolution for visible light passing through the plastic lens.

17. The goggle of claim 10 including vents located in the frame sections to vent external air pass an inner surface of the plastic lens to thereby reduce fogging on the plastic lens.

18. The goggle of claim 17 wherein the plastic lens is treated with an anti-fogging coating to further reduce fogging on the plastic lens.

19. The goggle of claim 10 wherein the plastic lens is formed of thermoplastic material consisting of polycarbonate or a cellulostic material.

20. The goggle of claim 10 wherein the plastic lens is formed of polycarbonate material which is injection molded in a spherical shape to create a spherical lens having a maximum thickness of 1.5 mm or less.

21. The goggle of claim 10 wherein the plastic lens is formed of cellulosic material which is extruded into a sheet of constant thickness to create a flexible cylindrical lens of constant thickness which curves when the mounting projections are in mating engagement with the lens mounting means of the frame.

22. A plastic lens member, wherein
the lens member is formed of a thermoplastic resin which incorporates dye material to tint the lens to produce a transmission curve for visible light over a range of wavelengths between 400 nm and 700 nm,
the transmission curve having a first peak of greater than a 20% transmission for a first range of wavelengths between 400 nm and 680 nm, at least one valley of reduced transmission for a second range of wavelengths adjacent to and above the first range, and a second peak of increased transmission greater than the first peak for a third range of wavelengths above the second range to improve contrast for visible light passing through the lens member.

23. The plastic lens member of claim 22 wherein the tint produces an average transmission through the lens member in the range of about 25% to 40%.

24. The plastic lens member of claim 22 wherein the thermoplastic resin is comprised of a polycarbonate material which is injected molded to form the lens member.

25. The plastic lens member of claim 24 wherein the polycarbonate material is injected molded into a spherical lens shape having a varying thickness from a center region towards the edge of the lens member.

26. The plastic lens member of claim 22 wherein the thermoplastic resin is comprised of a cellulosic material which is extruded into a sheet of fixed thickness to form the lens member.

27. The plastic lens member of claim 22 wherein the peaks and valley have a wavy shape related to the absorption bands of cones in a human eye retina so as to improve contrast resolution for visible light passing through the lens member.

28. The plastic lens member of claim 22 wherein the first range of wavelengths is about 400 nm to 450 nm and the first peak has about a 30% transmission or greater so as to correspond to a blue absorption band of cones in a human eye retina.

29. The plastic lens member of claim 22 wherein the lens member has an irregular peripheral shape with mounting projections forming a tinted plastic lens for attachment by at least the mounting projections to a goggle frame.

30. The plastic lens member of claim 22 wherein the lens member is a lens blank for the manufacture of a tinted plastic lens.

31. The plastic lens member of claim 22 wherein the transmission curve has a third peak of increased transmission greater than the first peak for a fourth range of wavelengths above the third range and another valley of reduced transmission for a fifth range of wavelengths adjacent to and above the fourth range whereby the lens member has at least three peaks and three valleys over the range of wavelengths between 400 nm to 700 nm.

32. A goggle comprising:

a frame having sections surrounding a wearer's face including a frame mounting section, a plastic lens formed of a thermoplastic resin and mountable in the frame mounting section in spaced relation in front of the wearer's face to define an interior space, the thermoplastic resin incorporating dye material to tint the plastic lens to transmit variable amounts of light over a range of wavelengths between 400 nm and 700 nm, the tinted plastic lens having a transmission curve with a wavy shape with peaks and valleys including a first peak of increased transmission located in the vicinity of 400 nm to 450 nm followed by a first valley of reduced transmission, a second level of increased transmission beyond the first peak, a third level of increased transmission beyond the first peak, and another valley of reduced transmission following the third level, wherein the first peak, second level and third level are respectively located in the vicinity of the blue, green and red absorption bands for cone photoreceptors in a human eye retina to thereby improve contrast for a wearer of the goggle.

33. The goggle of claim 32 wherein the first peak has a greater than 20% transmission located in the vicinity of 400 nm to 450 nm and the first valley has more than a 10% transmission decrease from the first peak.

34. The goggle of claim 32 wherein the second level corresponding to the vicinity of the green absorption band has a greater than 50% transmission located in the vicinity of 590 nm.

35. The goggle of claim 32 wherein the second level comprises a second peak and the third level comprises a third peak with an additional valley being located between the second peak and the third peak, and the first valley, additional valley and another valley each have more than a 10% transmission decrease from the preceding peak.

36. The goggle of claim 32 wherein the third level corresponding to the vicinity of the red absorption band comprises another peak having a greater than 50% transmission located in the vicinity of 630 nm.

37. The goggle of claim 32 wherein the another valley following the third level has more than a 40% transmission decrease from said third level.

38. The goggle of claim 32 wherein the plastic lens has an average transmission of light in the range of about 25% to 40%.

* * * * *